(12) United States Patent
Seeberger et al.

(10) Patent No.: US 7,406,349 B2
(45) Date of Patent: Jul. 29, 2008

(54) DYNAMIC TELEMETRY LINK SELECTION FOR AN IMPLANTABLE DEVICE

(75) Inventors: Michael Seeberger, Bayport, MN (US); Hui Li, Maple Grove, MN (US); Sylvia Quiles, Edina, MN (US); Raymond P. Kinnamon, St. Michael, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 374 days.

(21) Appl. No.: 10/914,638

(22) Filed: Aug. 9, 2004

(65) Prior Publication Data

US 2006/0030903 A1 Feb. 9, 2006

(51) Int. Cl.
*A61N 1/00* (2006.01)
(52) U.S. Cl. .............. 607/30; 607/31; 607/60; 128/903; 340/539.12
(58) Field of Classification Search .......... 607/60, 607/59, 30–32; 128/903; 340/539.12
See application file for complete search history.

(56) References Cited

U.S. PATENT DOCUMENTS

| | | | |
|---|---|---|---|
| 4,404,972 A | 9/1983 | Gordon et al. | |
| 4,441,498 A | 4/1984 | Nordling | |
| 4,519,401 A | 5/1985 | Ko et al. | |
| 4,562,841 A | 1/1986 | Brockway et al. | |
| 5,292,343 A | 3/1994 | Blanchette et al. | |
| 5,342,408 A | 8/1994 | deCoriolis et al. | |
| 5,683,432 A | 11/1997 | Goedeke et al. | |
| 5,694,952 A | 12/1997 | Lidman et al. | |
| 5,725,559 A | 3/1998 | Alt et al. | |
| 5,752,976 A | 5/1998 | Duffin et al. | |
| 5,807,397 A | 9/1998 | Barreras | |
| 5,843,139 A | 12/1998 | Goedeke et al. | |
| 5,861,019 A | 1/1999 | Sun et al. | |
| 6,044,485 A | 3/2000 | Dent et al. | |
| 6,169,925 B1 | 1/2001 | Villaseca et al. | |
| 6,200,265 B1 | 3/2001 | Walsh et al. | |
| 6,385,318 B1 | 5/2002 | Oishi | |
| 6,424,867 B1 * | 7/2002 | Snell et al. | 607/31 |
| 6,427,088 B1 | 7/2002 | Bowman, IV et al. | |
| 6,434,429 B1 | 8/2002 | Kraus et al. | |
| 6,443,891 B1 | 9/2002 | Grevious | |
| 6,463,329 B1 | 10/2002 | Goedeke | |

(Continued)

FOREIGN PATENT DOCUMENTS

EP 0607638 A2 7/1994

(Continued)

OTHER PUBLICATIONS

Quiles, S., "Automatic Power Control for a Radio Frequency Transceiver of an Implantable Device", U.S. Appl. No. 10/914,496, filed Aug. 9, 2004, 23 pgs.

(Continued)

*Primary Examiner*—Carl Layno
*Assistant Examiner*—Yun Haeng Lee
(74) *Attorney, Agent, or Firm*—Schwegman, Lundberg & Woessner, P.A.

(57) ABSTRACT

Communications with an implantable device are conducted using a physical telemetry link dynamically selected from multiple physical telemetry links based on selected criteria including, for example, bandwidth, security, data throughput, channel availability and reliability.

21 Claims, 5 Drawing Sheets

U.S. PATENT DOCUMENTS

| | | | |
|---|---|---|---|
| 6,470,215 | B1 | 10/2002 | Kraus et al. |
| 6,482,154 | B1 | 11/2002 | Haubrich et al. |
| 6,564,104 | B2 | 5/2003 | Nelson et al. |
| 6,564,105 | B2 | 5/2003 | Starkweather et al. |
| 6,574,510 | B2 | 6/2003 | Von Arx et al. |
| 6,585,644 | B2 | 7/2003 | Lebel et al. |
| 6,600,952 | B1 | 7/2003 | Snell et al. |
| 6,602,191 | B2 | 8/2003 | Quy |
| 6,622,050 | B2 | 9/2003 | Thompson |
| 6,687,546 | B2 | 2/2004 | Lebel et al. |
| 6,985,773 | B2 | 1/2006 | Von Arx et al. |
| 7,218,969 | B2 | 5/2007 | Vallapureddy et al. |
| 2002/0115912 | A1 | 8/2002 | Muraki et al. |
| 2002/0143372 | A1 | 10/2002 | Snell et al. |
| 2002/0147388 | A1 | 10/2002 | Mass et al. |
| 2003/0083719 | A1 | 5/2003 | Shankar et al. |
| 2003/0114897 | A1* | 6/2003 | Von Arx et al. ............... 607/60 |
| 2003/0114898 | A1 | 6/2003 | Von Arx et al. |
| 2003/0149459 | A1 | 8/2003 | Von Arx et al. |
| 2004/0030260 | A1 | 2/2004 | Von Arx et al. |
| 2004/0260363 | A1 | 12/2004 | Arx et al. |
| 2005/0204134 | A1 | 9/2005 | Von Arx et al. |
| 2005/0240245 | A1 | 10/2005 | Bange et al. |
| 2005/0283208 | A1 | 12/2005 | Von Arx et al. |
| 2006/0025834 | A1 | 2/2006 | Von Arx et al. |
| 2006/0030901 | A1 | 2/2006 | Quiles et al. |
| 2006/0030902 | A1 | 2/2006 | Quiles et al. |
| 2006/0030904 | A1 | 2/2006 | Qulies |
| 2007/0185550 | A1 | 8/2007 | Vallapureddy et al. |

FOREIGN PATENT DOCUMENTS

| | | | |
|---|---|---|---|
| WO | WO-03/053515 | A1 | 7/2003 |
| WO | WO-2005/099817 | A1 | 10/2005 |
| WO | WO-2006/020546 | A1 | 2/2006 |
| WO | WO-2006/020549 | A1 | 2/2006 |

OTHER PUBLICATIONS

Quiles, S., "Secure Remote Access for an Implantable Medical Device", U.S. Appl. No. 10/914,641, filed Aug. 9, 2004, 41 pgs.

Quiles, S., "Telemetry Switchover State Machine With Firmware Priority Control", U.S. Appl. No. 10/914,499, filed Aug. 9, 2004, 30 pgs.

"International Search Report and Written Opinion for Application No. PCT/US2005/028052, dated mailed Nov. 29, 2005", 12 pgs.

Healy, S. J., et al., "System and Method for Providing Secure Exchange of Sensitive Information With an Implantable Medical Device", U.S. Appl. No. 10/801,150, filed Mar. 15, 2004, 30 pgs.

Bange, Joseph E., et al., "Implantable Medical Device Telemetry With Adaptive Frequency Hopping", U.S. Appl. No. 11/456,937, filed Jul. 12, 2006, 35 pages.

Bange, Joseph E., et al., "Implantable Medical Device Telemetry With Periodic Frequency Hopping", U.S. Appl. No. 11/456,942, filed Jul. 12, 2006, 43 pages.

U.S. Appl. No. 10/071.255 Non-Final Office Action mailed Jan. 7, 2005, 6 pgs.

U.S. Appl. No. 10/071,255 Notice of Allowance mailed Jun. 15, 2005, 4 pgs.

U.S. Appl. No. 10/071,255 Response filed Apr. 7, 2005 Non-Final Office Acion mailed Jan. 7, 2005, 12 pgs.

U.S. Appl. No. 10/601,763, Non-Final Office Action dated Feb. 23, 2006, 9 pgs.

U.S. Appl. No. 10/601,763, Notice of Allowance dated Aug. 4, 2006, 8 pgs.

U.S. Appl. No. 10/601,763, Response to Non-Final Office Action filed May 23, 2006, 18 pgs.

U.S. Appl. No. 10/601,763, Supplemental Notice of Allowability dated Oct. 23, 2006, 4 pgs.

U.S. Appl. No. 10/801,070, Response to Non-Final Office Action filed Sep. 18, 2006, 15 pgs.

U.S. Appl. No. 10/801,070, Non-Final Office Action dated Feb. 6, 2006, 20 pgs.

U.S. Appl. No. 10/801,070, Non-Final Office Action dated Jun. 16, 2006, 6 pgs.

U.S. Appl. No. 10/801,070, Notice of Allowance dated Jan. 12, 2007, 7 pgs.

U.S. Appl. No. 10/801,070, Response to Non-Final Action filed Mar. 7, 2006, 14 pgs.

U.S. Appl. No. 10/914,449 Non-Final Office Action mailed May 29, 2007, 11 pgs.

U.S. Appl. No. 10/914,496 Final Office Action mailed May 23, 2007, 11 pgs.

U.S. Appl. No. 10/914,496 Non-Final Office Action mailed Dec. 5, 2006, 12 pgs.

U.S. Appl. No. 10/914,496 Response filed Mar. 5, 2007 to Non-Final Office Action mailed Dec. 5, 2006, 13 pgs.

U.S. Appl. No. 10/914,638 Final Office Action mailed Apr. 17, 2007, 10 pgs.

U.S. Appl. No. 10/914,638, Non-Final Office Action dated Oct. 18, 2006, 13 pgs.

U.S. Appl. No. 10/914,638, Response to Non-Final Office Action filed Jan. 18, 2007, 21 pgs.

U.S. Appl. No. 10/914,641 Final Office Action mailed Mar. 15, 2007, 10 pgs.

U.S. Appl. No. 10/914,641 Non-Final Office Action mailed Aug. 2, 2006, 9 pgs.

U.S. Appl. No. 10/914,641 Response filed Jan. 2, 2007 Non-Final Office Action mailed Aug. 2, 2006, 9 pgs.

U.S. Appl. No. 10/914,641 Response filed Jul. 16, 2007 final Office Action mailed Mar. 15, 2007, 9 pgs.

U.S. Appl. No. 11/039,200 Non-Final Office Action mailed Aug. 3, 2006, 10 pgs.

U.S. Appl. No. 11/039,200 Notice of Allowance mailed Dec. 15, 2006, 4 pgs.

U.S. Appl. No. 11/039,200 Response filed Nov. 2, 2006 to Non-Final Office Action mailed Aug. 3, 2006, 9 pgs.

Application Serial No. PCT/US2005/008521, International Preliminary Report on Patentability dated Sep. 28, 2006, 13 pgs.

Application Serial No. PCT/US2005/008521, International Search Report and Written Opinion dated Oct. 11, 2005, 19 pgs.

Application Serial No. PCT/US2005/028052, International Preliminary Report on Patentability dated Feb. 22, 2007, 8 pgs.

Application Serial No. PCT/US2005/028052, International Search Report and Written Opinion dated Nov. 29, 2005, 12 pgs.

"U.S. Appl. No. 10/071,255, Restriction Requirement mailed Sep. 28, 2004", 5 pgs.

"U.S. Appl. No. 10/071,255 Preliminary Amendment filed Oct. 5, 2005", 12 pgs.

"U.S. Appl. No. 10/071,255, Response and Preliminary Amendment filed Oct. 20, 2004 to Restriction Requirement mailed Sep. 28, 2004", 7 pgs.

"U.S. Appl. No. 10/025,223, Prosecution File History", (as of Oct. 23, 2007), 49 pgs.

"U.S. Appl. No. 10/914,496, Prosecution File History" (as of Oct. 30, 2007), 56 pgs.

"U.S. Appl. No. 10/914,641, Prosecution File History", (as of Oct. 24, 2007), 56 pgs.

"PCT Application No. PCT/US03/03748, International Search Report mailed Oct. 20, 2003", 5 pgs.

\* cited by examiner

DYNAMIC TELEMETRY LINK SELECTION FOR AN IMPLANTABLE DEVICE

CROSS-REFERENCE TO RELATED DOCUMENTS

This document is related to U.S. patent application Ser. No. 10/914,449, entitled "TELEMETRY SWITCHOVER STATE MACHINE WITH FIRMWARE PRIORITY CONTROL," filed Aug. 9, 2004 by Quiles et al. (Attorney Docket 00279.772US1) and is incorporated herein by reference.

This document is related to U.S. patent application Ser. No. 10/914,641, entitled "SECURE REMOTE ACCESS FOR AN IMPLANTABLE MEDICAL DEVICE," filed Aug. 9, 2004 by Quiles (Attorney Docket 00279.771US1) and is incorporated herein by reference.

TECHNICAL FIELD

This document pertains generally to implantable devices, and more particularly, but not by way of limitation, to telemetry link selection for an implantable device.

BACKGROUND

Implantable devices typically communicate using an inductive telemetry link. Inductive telemetry refers to communications involving a loop antenna of an external device inductively coupled with a loop antenna of the implantable device.

Communication inefficiencies associated with inductive telemetry impair the delivery of medical care. Inefficiencies include low bandwidth and limitations associated with the requirement for close physical proximity. Improved telemetry systems are needed.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed herein.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The examples may be combined, other examples may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Introduction

An implantable device allows exchange of data with an external device using multiple telemetry circuits to communicate using different physical links having different characteristics. In one example, the implantable device includes a near field telemetry circuit which communicates using a near field physical link and a far field telemetry circuit which communicates using a far field physical link. The near field physical link and the far field physical link differ in terms of bandwidth, communication range, power consumption, security and other factors.

One example of an implantable device includes both a far field radio frequency telemetry system, which provides broadband and long range communication, and a near field inductive telemetry system, which provides short range communication while drawing a relatively low current consumption. The far field radio frequency telemetry link and the near field inductive telemetry link are examples of physical links.

The selection of the physical link is determined by external device based on predetermined selection criteria. In one example, as between a radio frequency telemetry link and an inductive telemetry link, the radio frequency telemetry link is faster and therefore preferred over the inductive telemetry link. In one example, the data to be communicated may be sensitive or confidential and thus, security is of greater concern than speed. As another example, a user selection may include a preference for one telemetry link or a hierarchy of telemetry links. Other factors, including data throughput rate, are also contemplated for selecting one physical link rather than another.

In one example, the physical link is selected by a procedure of alternately attempting to establish communications using one physical link followed by attempting to establish communications using a second physical link. In one example, external device includes programming, circuitry or logic to select the physical link and the implantable device functions as a slave and adjusts accordingly.

A controller coupled to the telemetry circuits of the implantable device selects one of the multiple telemetry circuits for communicating with an external device based on an instruction or command received from the external device. In various examples, the selection of the telemetry circuit, and therefore, the physical link, is determined by at least one parameter or other data provided by the implantable device, the external device or by a combination of the implantable and external device. For example, a parameter corresponding to a battery condition of the implantable device can affect the physical link selection.

Data is communicated between the external device and the implantable device in a unit of data referred to as a data frame (also referred to as a frame). A frame exchange refers to the conveyance of the frame. In one example, a frame exchange must start and finish on the same physical link. A frame can include, for example, a frame such as an instruction to change a value stored in implantable device 110, deliver a particular therapy, begin a test, write a parameter, take an action or read a storage register.

In one example, two modes are available for communicating between the implantable device and the external device. In one mode, referred to as real time telemetry, data is continuously streamed from the implantable device to the external device. In real time telemetry, the data can include, for example, electrocardiogram data and physical link switching can occur right before the start of a new frame exchange (including programmer re-tries) or if the current link becomes unavailable (after the loss of a signal for a period of time). In another mode, referred to as command telemetry, data from the external device is sent to the implantable device. The data can include an instruction or other command and the external device always expects responses to commands on the same telemetry link in which they were transmitted.

Structure

Figure 1:
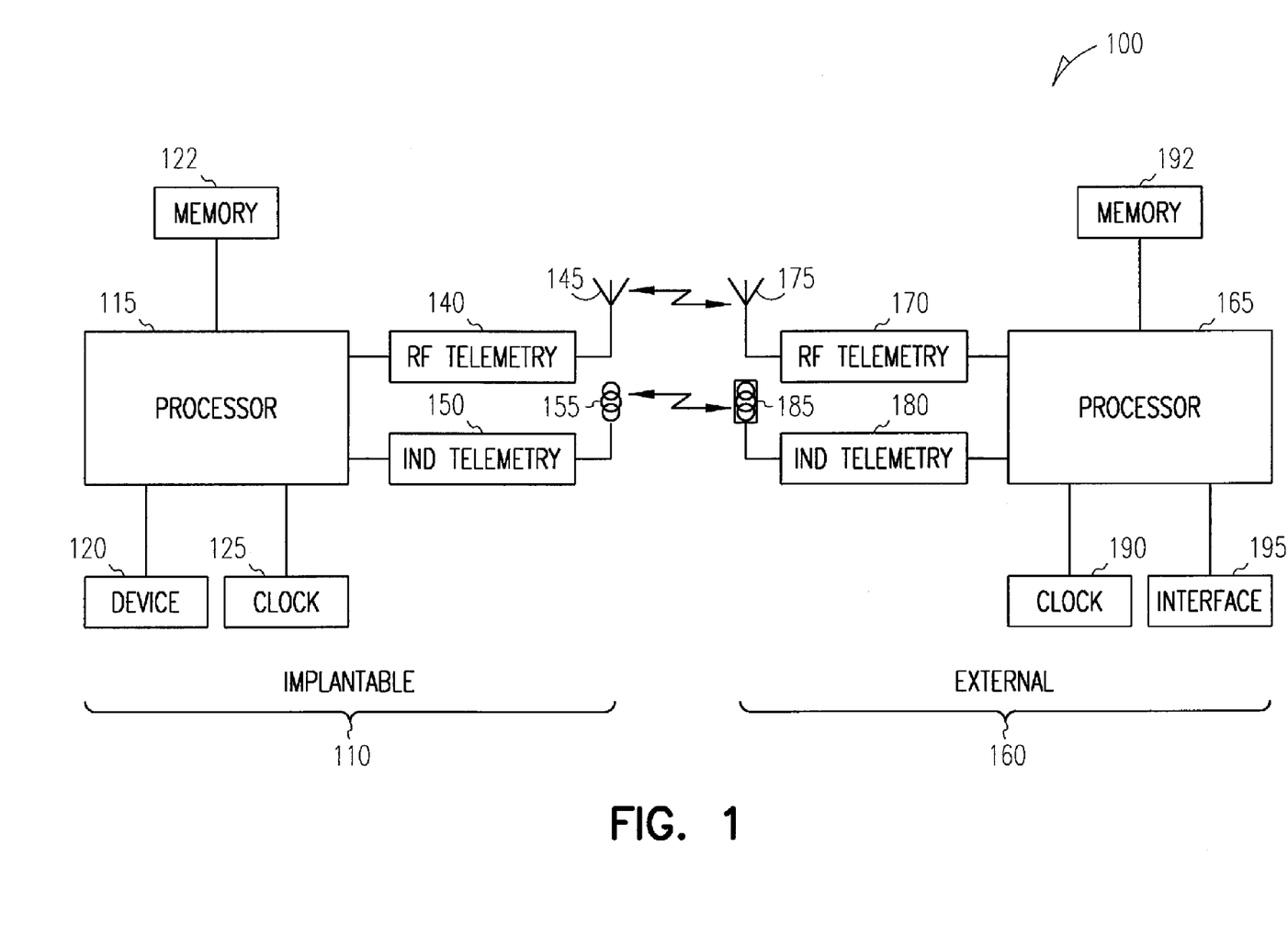
FIG. 1 includes an illustration of an implantable device in communication with an external device.

FIG. 1 illustrates system 100 including implantable device 110 and external device 160, each having dual telemetry circuits.

Implantable device 110 includes processor 115 coupled to device 120. Device 120, in various examples, includes a monitor circuit and a therapy circuit. Exemplary therapy circuits include a pulse generator (such as a pacemaker, a cardiac rhythm therapy device, a heart failure or cardiac resynchronization device, a cardioverter/defibrillator, a pacer/defibrillator) and a drug delivery device (such as an implantable drug pump). An exemplary monitor circuit includes electrodes or other sensors coupled to a heart to monitor cardiac function or other physiological stimulus. In addition, processor 115 is coupled to radio frequency telemetry circuit 140 and inductive telemetry circuit 150. Radio frequency telemetry circuit 140 includes a transceiver coupled to radio frequency antenna 145. Antenna 145 is configured to generate and receive far field signals. In one example, power delivered to radio frequency telemetry circuit 140 is controlled or managed based on instructions received from processor 115.

Inductive telemetry circuit 150 is coupled to inductive antenna 155. In one example, inductive telemetry circuit 150 includes a continuously powered transceiver. Antenna 155 is configured for near field transmission and reception, and, in one example, includes a loop antenna.

Implantable device 110 includes clock 125 coupled to processor 115. Clock 125 provides a timing signal for the benefit of processor 115. Memory 122, also coupled to processor 115, provides storage for data, parameters or instructions. In various examples, memory 122 includes read-only memory, random access memory or other storage and in one example, is remotely programmable.

External device 160 includes processor 165 coupled to interface 195. Interface 195, in various examples, includes a display monitor, a printer, a keyboard, a touch-sensitive screen, a cursor control, a speaker, a microphone, a storage device and a network interface device. External device 160, in one example, includes a programmer for use by a physician or other medical personnel at the time of implantation as well as during follow-up visits. As a programmer, external device 160 allows interrogation as well as programming of implantable device 110, and accordingly, includes a user-accessible interface. External device 160, in one example, includes a remote interrogation device (sometimes referred to as a repeater) which allows connecting with a bi-directional communication network such as a local area network (Ethernet), a wide area network (such as the Internet) or telephone lines in a home (plain old telephone service via the public switched telephone network). In addition, processor 165 is coupled to radio frequency telemetry circuit 170 and inductive telemetry circuit 180. Radio frequency telemetry circuit 170 includes a transmitter and receiver (also referred to as a transceiver) coupled to radio frequency antenna 175. Antenna 175, like antenna 145, is configured to generate and receive far field signals.

Inductive telemetry circuit 180 includes a transceiver coupled to inductive antenna 185. Antenna 185, in one example, is part of a hand-operable device sometimes referred to as a wand. The wand enables inductive communications over a short range of approximately 6 inches. Antenna 185, like antenna 155, is configured to generate and receive near field signals and, in one example, includes a loop antenna.

External device 160 includes clock 190 coupled to processor 165. Clock 190 provides a timing signal for the benefit of processor 165. Memory 192, also coupled to processor 165, provides storage for data, parameters or instructions. In various examples, memory 192 includes read-only memory, random access memory, removable or non-removable media or other storage and in one example, is programmable.

In various examples, electrical power for external device 160 is provided by a portable power supply, such as a battery, or by a metered line service. When powered by a battery, external device 160 can be configured for handheld use. External device 160 can communicate using a wired or wireless communication channel.

Method

Figure 2:
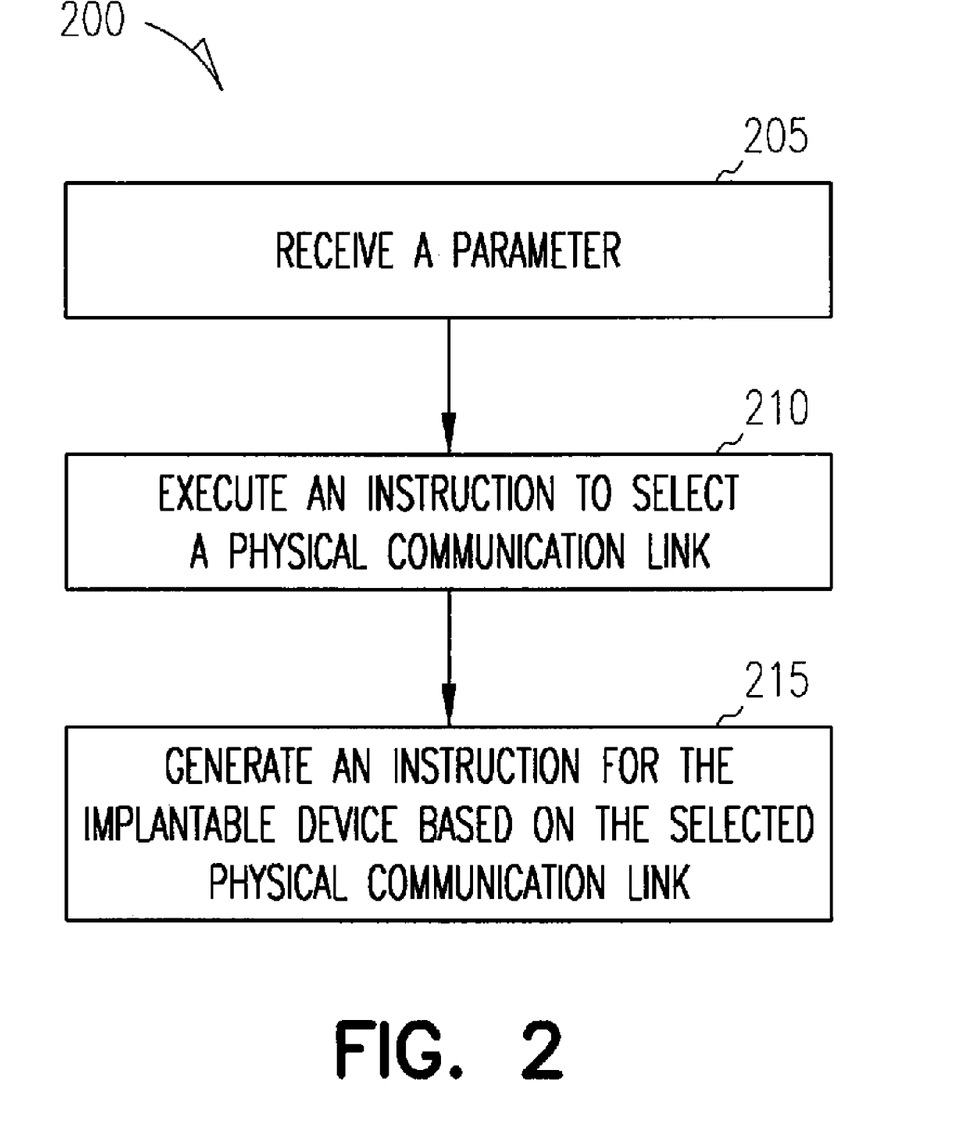
FIGS. 2, 3, 4 and 5 include illustrations of flow charts for selecting a physical link.

In one example, system 100 operates according to flow chart 200 as shown in FIG. 2. At 205, external device 160 receives a parameter that is used in determining the physical link for the communication session. In various examples, the parameter is received by interface 195 coupled to external device 160. For example, a user accessible data entry device, such as a mouse, keyboard, touch sensitive screen, memory device, audio transducer or other component can receive a user input. In one example, external device 160 is coupled to a communication network, such as an Ethernet, local area network or the Internet and configured to receive data corresponding to the parameter.

The parameter received at 205 is used to select the physical link. In various examples, the physical link is determined based on considerations including, but not limited to security, bandwidth, reliability and noise. In one example, the physical link selection parameter changes over time. In one example, the parameter used to select the physical link can change such that, at one time, the physical link is determined based on a security measure and at another time, the physical link is determined based on a reliability measure. In one example, a combination of two or more criteria is used in generating a parameter used to select a physical link.

The selection of the physical link can be based on various criteria. In one example, communication system 100 is configured with a preference for one particular link rather than another. For example, a radio frequency physical link may exhibit a larger bandwidth and therefore, is favored over an inductive physical link. Accordingly, the physical link can be selected based on a system-dependent parameter.

In one example, the parameter relates to a user specified preference or priority among a number of physical links. For example, the user may indicate that a radio frequency physical link is given first priority and an optical physical link is given a second priority.

In one example, the parameter relates to a measure of reliability for a particular physical link. For example, an inductive physical link may exhibit greater reliability than a radio frequency physical link.

In one example, the parameter relates to a measure of security. The measure of security, in various examples, corresponds to different levels of, or to the use of different passwords. For example, when transmitting the patient's name or other patient health information, a physical link offering a particular level of security may be selected. Accordingly, for patient health information, one example provides that an inductive physical link is more secure than a radio frequency physical link. As another example, sensitive or important data is communicated using a secure physical link without regard for communication speed or other performance criteria. In one example, data stored in implantable device 110 is read using an inductive physical link. In one example, the data is encrypted by a processor implementing an encryption algorithm and the encrypted data is communicated using a radio frequency physical link.

In one example, data generated by implantable device 110 is used to select a physical link. For example, the data generated by implantable device 110 may indicate that the battery is approaching the end of its useful life. Accordingly, a measure of the battery capacity is used in one example to generate a parameter that is used in selecting the physical link for communicating. A low current consumption transceiver is given preference over a transceiver that draws greater current consumption. In one example, an inductive telemetry circuit draws less current than that of a radio frequency transceiver. In one example, the data generated by implantable device 110 is used in conjunction with other criteria in generating a parameter for selecting a physical link. In one example, a measure of power consumption is used in generating the parameter.

In one example, the physical link selection parameter is generated based on a measure of data throughput or based on a measure of communication channel performance. For example, a speed or bandwidth measurement is used in selecting a communication channel.

In one example, the physical link exhibiting a greater bandwidth, data throughput, security or reliability enjoys priority over another telemetry link. In one example, the radio frequency telemetry link is faster than an inductive telemetry link, and therefore the radio frequency telemetry link enjoys priority. In other examples, a different telemetry link may have priority over the radio frequency telemetry link.

In one example, an externality (measured or detected) is used in selecting a physical link. For example, an externality, such as an excessively noisy environment, may compel the use of inductive physical link rather than radio frequency physical link. The externality may affect the error rate, reliability, security, data throughput, channel availability or other parameter associated with a telemetry link.

The physical link describes the channel or band by which implantable device 110 and external device 160 conduct communications. Exemplary physical links include inductive telemetry, radio frequency telemetry, infrared, optical, acoustical and magnetic.

For a particular physical link, any of a variety of encoding/decoding or communication protocols may be used. For example, modulation techniques such as frequency shift keying or quadrature phase shift keying can be applied using an inductive physical link as well as a radio frequency physical link.

At 210, external 160 device executes one or more instructions, using processor 165, to determine a physical link for communicating with implantable device 110. In one example, the instructions implement an algorithm that includes a comparison of two physical links. In one example, the instructions implement an algorithm that calculates a factor, such as signal quality, signal to noise ratio, bandwidth or other parameter which is used in selecting a physical link.

At 215, processor 165 generates an instruction for delivery to implantable device 110 which specifies the physical link. In one example, the instruction is encoded in the form of a signal or a missing signal in a series of signals. In one example, a series of synchronization (or sync) signals are transmitted by external device 160 and implantable device 110 replies with an alignment signal to indicate that the devices are synchronized. In one example, external device 160 signals implantable device 110 of a change in the physical link by dropping a predetermined number of sync signals in a series of sync signals.

Figure 3:
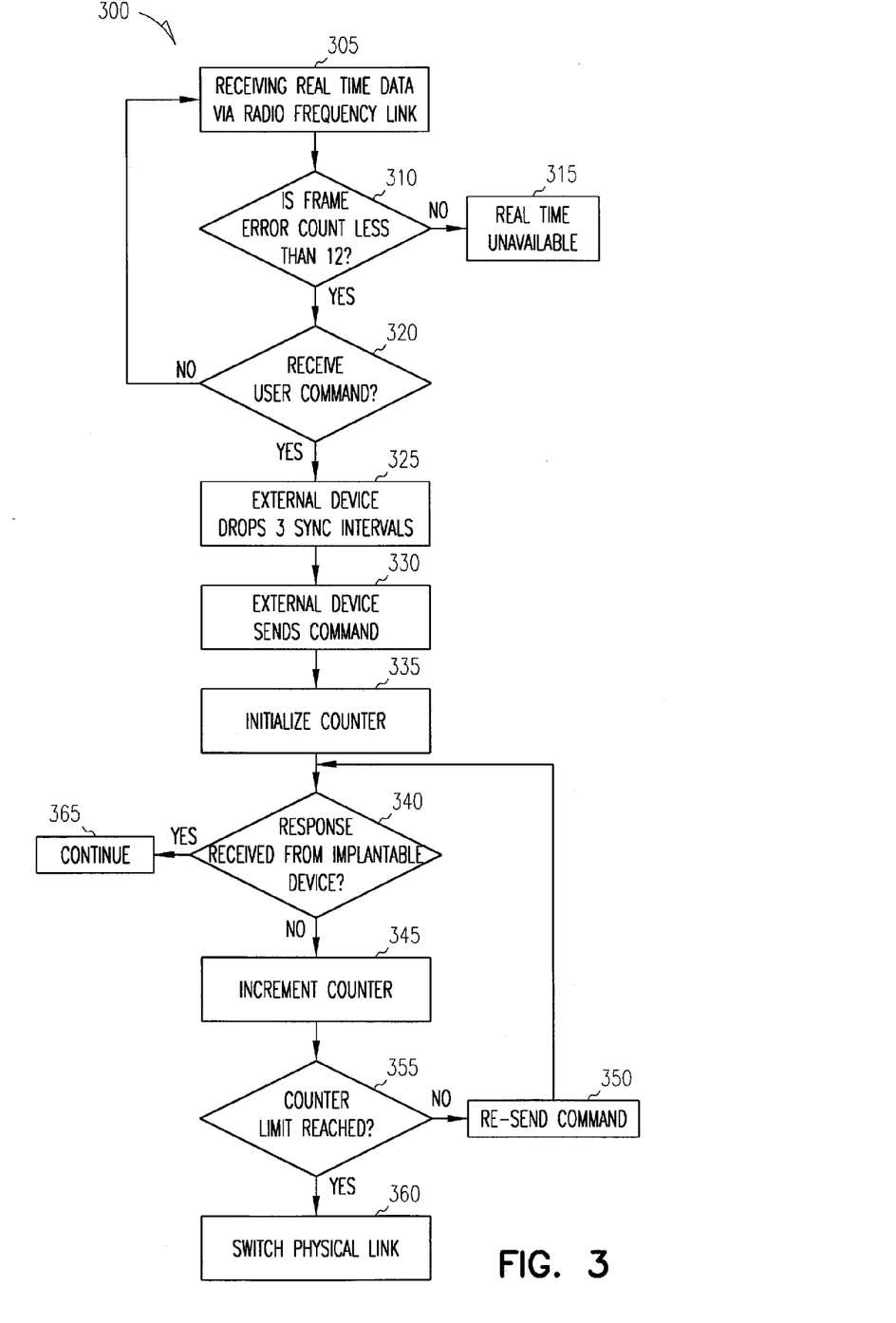

FIG. 3 illustrates method 300 including an example of an algorithm for switching physical links. At 305, external device 160, which can include a remote interrogation device, a programmer or other device, is receiving real time data through the radio frequency physical link. In one example, the radio frequency physical link remains available as long as the frame error count is less than 12 consecutive frame errors, as shown at 310. At 315, if the frame error count exceeds a predetermined value, then real time communications are no longer available on this link. In the example illustrated, a query is presented to determine if the user entered command is received, at 320, which triggers the transition from real time mode to command mode. The user entered command, in various examples, includes a command to perform an action such as reading or writing data to a register. While synchronized, external device 160 continues to periodically send a synchronization signal.

If, at 320, the user entered command is not received, then processing returns to 305 where the radio frequency telemetry link is used.

Following receipt of the user entered command, external device 160 drops three consecutive sync signals, as shown at 325. Implantable device 110 recognizes the absence of the three consecutive sync signals as a signal to suspend transmission of real time data and await a command from external device 160. In addition, upon dropping the three consecutive sync signals, the frame error count value is reset when real time telemetry is terminated.

At 330, external device 160 transmits a command to implantable device 110. In one example, external device 160 monitors for a response to the transmitted command and a counter is used to limit the number of attempted re-transmissions. At 335, a counter of external device 160 is initiated. At 340, a query is presented to determine if a response was received from implantable device 110. In one example, a valid response will arrive prior to a predetermined response timeout value. At 340, if a response is not received prior to expiration of the response timeout value, then, processing continues to 345 where the counter is incremented. At 355, a query is presented to determine if the counter has reached a predetermined limit value. If the limit value has not been met, then, as shown at 350, the command is re-sent by external device 160 and the query at 340 is repeated. If the counter limit is reached and no response was received from implantable device 110, as shown at 360, then external device 160 switches the physical link from the radio frequency link to an inductive link. If, on the other hand, a response is received from implantable device 110, then, as shown at 365, processing and communications continue using the radio frequency link.

In one example, if no reply is received from implantable device 110 after seven attempts, then external device 160 will attempt to switch telemetry links. In the example illustrated by method 300, the physical link transition is triggered after having attempted and failed using the same exchange for seven times. In one example, the waiting time to switch is approximately one second.

Figure 4:
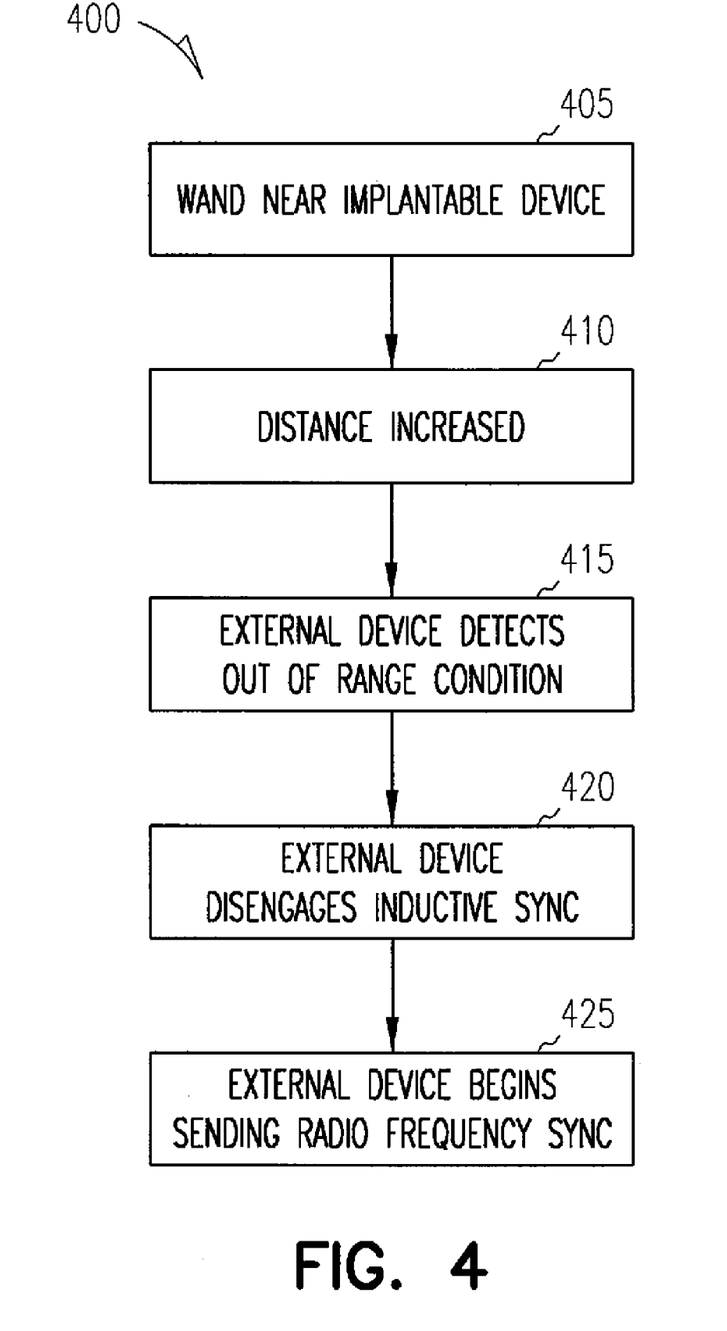

FIG. 4 illustrates method 400 including an example of an algorithm for switching physical links. At 405, a wand coupled to external device 160 is placed near implantable device 110 during a time when real time transmissions are being continuously received through the inductive link. If the distance between the wand and implantable device 110 is increased to exceed the communication range, as shown at 410, then external device 160 will detect this by noting the absence of alignment signals in four consecutive sync intervals and signaling the out of range condition, as shown at 415. Upon detecting the out of range condition, external device 160 will drop the inductive synchronization signals, as shown at 420, and allow implantable device 110 to disengage from the inductive sync state. In one example, external device 160 will disengage from the inductive link and resume real time telemetry by sending radio frequency sync signals, as shown at 425, after approximately 100 milliseconds.

Establishing radio frequency telemetry entails sending periodic syncs from external device 160 using the radio frequency physical link. In one example, external device 160 will maintain the radio frequency physical link for as long as the frame error count is less than 12. In one example, the real time transmission is not a frame exchange. In one example, the loss of the inductive physical link serves to trigger the telemetry link switching.

Figure 5:
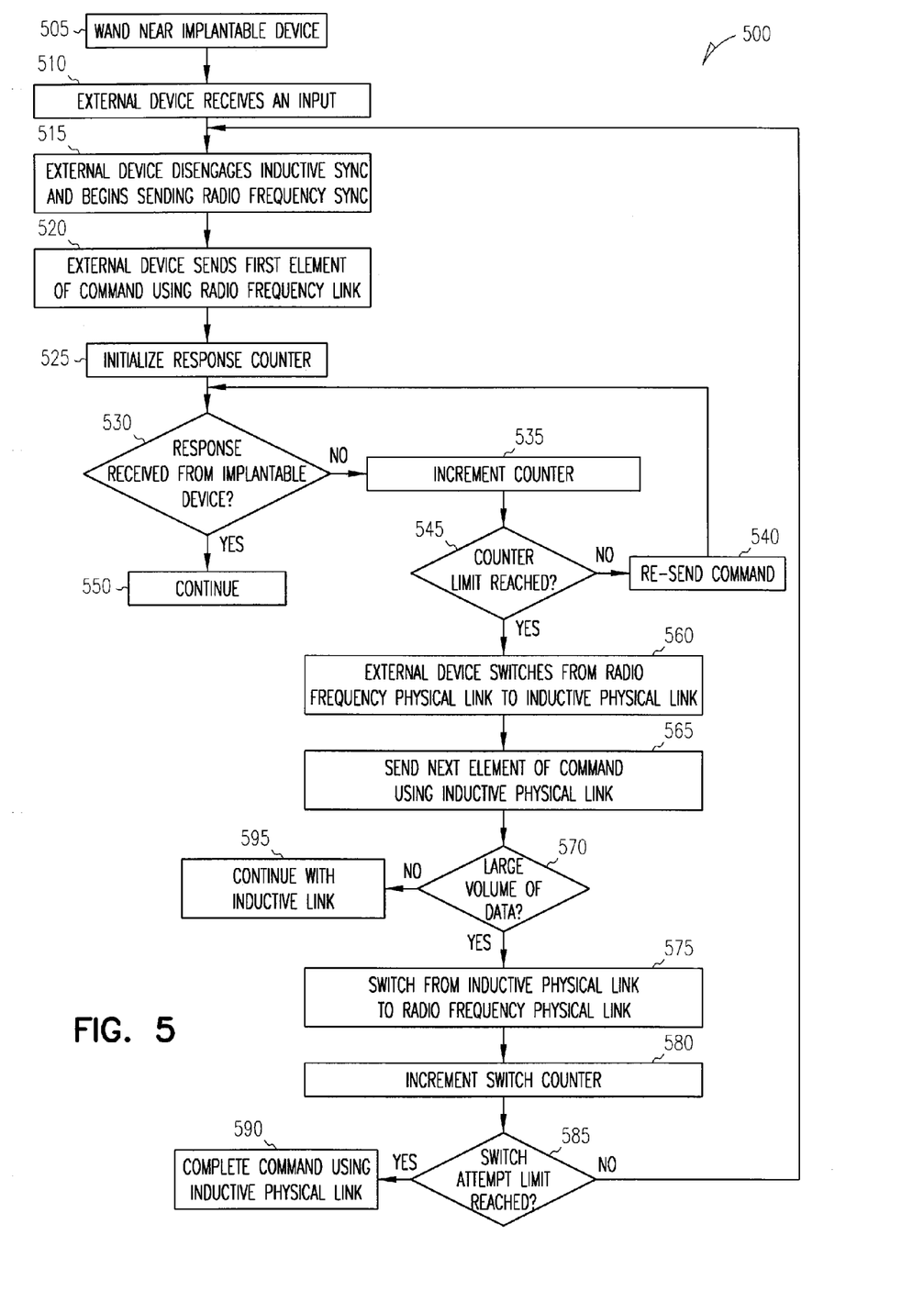

FIG. 5 illustrates method 500 including an example of an algorithm for switching physical links. At 505, a wand coupled to external device 160 is placed near implantable device 110 during a time when real time transmissions are being continuously received through the inductive link. At 510, external device 160 receives an input which forms the basis of a command for implantable device 110. The input can be received by a user input device or by a connection to a communication network. In one example, the user selects an action for communicating to implantable device 110. Upon receiving the input for transmission to implantable device 110, external device 160 will switch from the inductive physical link to the radio frequency physical link since external device 160 favors the radio frequency physical link. In one example, external device 160 will indicate that the communication channel, or band, is in use if the channel is unavailable.

At 515, external device 160 drops inductive sync signals and begins sending radio frequency sync signals. In addition, at 520, external device 160 sends the first element of the command in the telemetry sequence using the radio frequency physical link.

At 525, a response counter is initialized to monitor the number of communication attempts. In one example, a timer is provided to monitor the duration of attempted communications. At 530, a query is presented to determine if a response is received from implantable device 110. If a response is received, then, at 550, processing continues with the transmission and reception of additional elements of the command.

As shown at 535, if a response is not received, then the response counter is incremented followed by a query to determine if the maximum number of attempts has been reached. If the count remains below the counter limit, then the element of the command is re-sent at 540, followed by the query at 530 to determine if implantable device 110 has responded. In one example, external device 160 attempts to send the command up to seven times using the radio frequency physical link.

After having reached the counter limit at 545, processing continues at 560 where external device 160 then switches the physical link and returns to the inductive physical link. The counter limit may have been reached, for example, by a failure of a cyclic redundancy check code in the response. If the inductive telemetry wand remains in range of implantable device 110, then external device 160 completes the command by using the inductive physical link, as shown at 565.

In one example, a particular telemetry link is preferred for use with those commands involving the transmission of a large volume of data and the most recently used, or current, telemetry link is used for transmissions involving a small volume of data. The overhead involved in attempting to select a telemetry link is not warranted for transmissions involving a small volume of data.

At 570 a query is presented to determine if the next element in the command calls for transmitting a large volume of data. If the next element in the command does not call for transmitting a large volume of data, then external device 160 remains in the inductive telemetry link, as shown at 595. If the next element in the command calls for transmitting a large volume of data, then external device 160 attempts to transmit the command using the radio frequency telemetry link, as shown at 575. The switch to the radio frequency physical link shown at 575 is the second selective link switch attempt.

If external device 160 unsuccessfully attempts a predetermined number of inductive physical link to radio frequency physical link switches, then external device 160 will continue with the inductive physical link and complete the telemetry transaction without any further attempts to switch physical links. In one example, the predetermined number of unsuccessful attempts is five, however more or less than five are also contemplated.

A counter monitors the number of telemetry switches and prevents excessive attempted switching. At 580, the counter is incremented after the switch noted at 575. At 585, a query is presented to determine if the counter has reached a limit. If the limit is met, then at 590, transmission of the command is completed using the inductive physical link. If the limit is not met, then processing continues at 515 where transmission of the next element of the command is attempted using the radio frequency physical link.

If the inductive physical link is unavailable (for example, the distance between implantable device 110 and external device 160 is beyond the supported communication range) at any time prior to completing the transmission of the full user request (for example, a full interrogation of implantable device 110), then external device 160 will switch repeatedly between the inductive and radio frequency physical link until one becomes available or until the user request is cancelled or aborted.

In one example, external device 160 can be forced to switch to the radio frequency physical link by, for instance, moving the inductive wand out of range of implantable device 110. In one example, external device 160 can be forced to switch to the inductive physical link by moving the inductive wand into range of implantable device 110. The act of positioning a wand near the implantable device, in one example, indicates a user preference to select a particular telemetry link. In one example, the user can terminate the radio frequency telemetry session by initiating a new interrogation using a telemetry wand of another external device.

An inductive physical link override occurs if a series of inductive syncs are started within 100 milliseconds of the last radio frequency sync. In one example, implantable device 110 will wait for at least three inductive syncs before processing a frame received using the inductive physical link.

In one example, to switch from an inductive physical link to a radio frequency physical link, implantable device 110 will look for a period of at least 100 milliseconds during which no inductive syncs are received before processing a frame received using the radio frequency physical link.

In one example, external device 160 transmits an express instruction to select a particular telemetry link and implantable device 110 responds by selecting the specified telemetry link.

Exemplary Alternatives

In one example, the telemetry links available include an inductive physical link and a radio frequency physical link. In one example, more than two telemetry links are available. In one example, the present system selects a particular physical link from the available links including two radio frequency physical links (each operating using different protocols or different frequencies) and an inductive physical link.

If implantable device 110 and external device 160 are within inductive communication range, then attempting to establish a radio frequency link in a noisy environment can be wasteful of power resources and time. Accordingly, and under these conditions, external device 160 does not attempt to establish a radio frequency telemetry link. In one example, implantable device 110 attempts to use the radio frequency link for a predetermined amount of time and if it fails to establish a telemetry link, then implantable device 110 reverts to the inductive link. If, in turn, the inductive telemetry link is unavailable, then external device 160 will sequentially switch back and forth between the inductive and radio frequency telemetry links.

Furthermore, if a first telemetry link is unavailable, or does not provide satisfactory performance, then communications are attempted using a second telemetry link. In one example, a procedure is executed for attempting to establish communications using a plurality of telemetry links.

Unsuccessful attempts to establish communications may negatively impact the user's experience by introducing additional delay. The procedure for selecting a telemetry link can affect the user's perception of system performance.

In one example, a processor of external device 160 executes instructions to first attempt to establish communications with an implantable device using a first physical link and, if unsuccessful, then attempt to establish communications with implantable device 110 using a second physical link. If the second physical link is also unsuccessful, then, in one example, external device 160 repeats the sequence of attempts using the first physical link followed by the second physical link. In one example, external device 160 attempts to establish a communication session with an implantable device using a physical link selected based on the physical link used most recently in a previous communication session. For example, if the radio frequency telemetry circuit was most recently used, then a later communication session with the same devices will be first attempted using the radio frequency telemetry circuit.

In one example, if external device 160 experiences an error rate in excess of a first particular value, then external device 160 terminates further attempts to establish a radio frequency telemetry session and attempts to establish an inductive telemetry session. In one example, external device 160 suspends attempts to establish a radio frequency telemetry link if a frame error count exceeds a particular value in a period of time or after a predetermined number of synchronization signals. In one example, the predetermined number of synchronization signals is 12 with each signal having a duration of approximately 8 milliseconds.

In one example, if the inductive telemetry wand is out of range of implantable device 110, or the inductive telemetry circuit is otherwise not available, then after a second particular value of time, external device 160 terminates efforts to establish an inductive communication session and attempts to establish a radio frequency telemetry session. In one example, the second particular value is of a shorter duration than the first particular value. In one example, the second particular value is four synchronization periods.

In one example, the durations corresponding to the first and second particular values are determined by the type of communication session to be conducted. In one example, the system provides both a real time communication session and a command session. In a real time communication session, data generated by the implanted device (for example, electrocardiogram data) is communicated to external device 160 in a continuous data stream and rendered as a scrolling image on a display or stored for later processing and display. In a command session, external device 160 communicates an instruction or command to implantable device 110. In a real time communication session, the durations are shorter than that of a command session.

In one example, external device 160 is operating in either a command mode or a real time mode. In other words, if external device 160 is not actively sending a command to implantable device 110 during a communication session, then real time data is being received.

In one example, external device 160 will terminate attempts to establish a radio frequency telemetry link and attempt to establish an inductive telemetry link when (a) there have been 12 consecutive frames during which implantable device 110 has not responded or (b) a cyclic redundancy code indicates an error.

In the command mode, external device 160 has data, an element, an instruction or command to communicate to implantable device 110. In command mode, external device 160 initially attempts to communicate using a radio frequency telemetry link. If implantable device 110 is non-responsive to the radio frequency command, then external device 160 conducts a series of repeated attempts for a particular number of times. If, for example, after seven attempts to establish a radio frequency telemetry link, then external device 160 terminates further attempts using radio frequency telemetry and attempts to establish communications using an inductive telemetry link. In one example, external device 160 completes a predetermined number of attempts to establish an inductive telemetry link after which external device 160 terminates further attempts using inductive telemetry and attempts to establish a radio frequency telemetry link. In one example, external device 160 will repeat the sequence of attempting to establish a telemetry link using radio frequency telemetry and inductive telemetry.

In one example, external device 160 initially attempts to establish a radio frequency telemetry link regardless of whether a wand coupled to external device 160 is located near implantable device 110. Assuming noise or another interfering signal precludes satisfactory use of radio frequency telemetry, external device 160 switches and attempts to establish an inductive telemetry link.

In one example, and when available, external device 160 will use the radio frequency telemetry link. Accordingly, selective link switching, from inductive telemetry to radio frequency telemetry, will occur even when the inductive link is available. In one example, the user specifies a preferred telemetry link which may be different than a radio frequency telemetry link.

In one example, a frame exchange starts and ends on the same physical link. Selective link switching will occur just before the start of a new telemetry sequence, except when the same telemetry sequence is repeated multiple times for a single user request (e.g., a command to read selected memory registers). In this case, inductive physical link to radio frequency physical link selective switching will occur before the first sequence is issued. Selective link switching from inductive physical link to radio frequency physical link can also occur in the middle of a telemetry sequence. In one example, this form of selective link switching can occur up to a predetermined number of times (for example, five times) during the telemetry sequence. In one example, a failed attempt at selective switching to radio frequency physical link is counted towards the maximum number of selective link switching attempts of five. This limits the delay to respond to the user and makes it predictable for long sequences (e.g. initial interrogation) when the inductive physical link is available but the radio frequency physical link is not.

During real time telemetry, link switching occurs if the current telemetry link in use is lost (assuming there is no other system constraint). If the current telemetry link in use is the inductive link, the telemetry link is lost when the telemetry wand is out of range. External device 160 then drops inductive syncs for a predetermined number of intervals (in one example, 12 intervals) to allow implantable device 110 to disengage from its inductive sync state. When implantable device 110 is in the inductive sync state, a predetermined period of time (in one example, 100 milliseconds) is introduced before transitioning to the radio frequency physical link. If the wand has been out of range for at least a predetermined period of time (in one example, 100 milliseconds), then the transition can occur immediately. If the current telemetry link in use is the radio frequency physical link, then determining when the telemetry link is lost is based on frame error counts.

If the radio frequency physical link is not available for telemetry transactions, then external device 160 will try to start a frame exchange using the inductive link. When a channel is available (whether radio frequency or inductive), a frame exchange is tried twice on the inductive link or seven times on the radio frequency link before attempting to switch telemetry links.

To determine channel availability, external device 160 generates a measure of quality. Examples of a measure of quality include a frame error count and a bit error rate. A frame error is counted when (a) a frame cyclic redundancy check code fails (as determined by a cyclic redundancy check code error response frame received from implantable device 110 or if the cyclic redundancy check code of the received frame fails); (b) the frame is not received when expected (as determined during real time if a data frame is not received during the current sync interval, such as during a frame exchange if a data frame is not received before the response timeout expires); or (c) the frame received does not match the expected values in the frame format (for example the frame is that of another system within communication range). No frame is declared when either a command response time out occurs or a real time data frame is not received in the current synchronization interval.

In one example, external device 160 evaluates a telemetry link by using a spectrum analyzer. The spectrum analyzer provides a measure of the quality of a channel. External device 160 executes a method whereby the channel quality is sampled using the spectrum analyzer and generates a measure of quality without first attempting to communicate using that particular telemetry link.

In one example, the frame error count is not incremented more than once per sync interval during real time or more than once per command during frame exchanges. The frame error count is reset anytime a valid frame is received (as determined by the above conditions) or upon switching telemetry links.

In one example, selective link switching is limited to no more than five failed attempts per every user initiated telemetry transaction. In one example, external device 160 switches telemetry links if any of the following conditions occur:

1. Radio frequency physical link to inductive physical link: frame error count for the radio frequency physical link indicates that 12 consecutive frame errors were detected during real time.

2. Inductive physical link to radio frequency physical link: telemetry wand is out of range while using the inductive link during real time.

3. Radio frequency physical link to inductive physical link: a frame exchange in the radio frequency physical link fails after being tried seven times.

4. Inductive physical link to radio frequency physical link: a frame exchange in the inductive physical link fails after being tried twice.

5. Inductive physical link to radio frequency physical link (selective link switching): while using the inductive physical link, before the start of a telemetry sequence or the first of a repeated set of the same sequence (e.g., a command to read selected memory registers).

6. Inductive physical link to radio frequency physical link (selective link switching): while using the inductive physical link, before the start of a read or write command (read logical/ physical, write logical, read history) during a telemetry sequence or a repeated set of the same sequence (e.g., a command to read selected memory registers).

In one example, external device 160 continues to alternate attempts between both telemetry links until one becomes available or the user cancels the current action request. In one example, if real time is enabled, then telemetry link switching may continue indefinitely.

In one example, implantable device 110 and external device 160 have a slave/master relationship where external device 160 is always the master and implantable device 110 is always the slave.

In one example, the system is limited to one active radio frequency communication session in a given radio frequency channel. The session limit ensures that a new session just starting does not interfere with another active session. Radio frequency sync signals and radio frequency frames include a header which allows external device 160 to detect other sessions in progress. External device 160 is responsible for enforcing the radio frequency session limitation of one active radio frequency communication session in a given radio frequency channel. Once a session is initiated, implantable device 110 retains the session access code until the session is terminated. In one example, implantable device 110 supports multiple active sessions at a time.

In one example, external device 160 will monitor radio frequency traffic for a period of time (200 milliseconds in one example) before establishing a radio frequency communication link. If external device 160 includes a programmer, and if radio frequency traffic is noted, then external device 160 communicates using the inductive link. If external device 160 includes a remote interrogation device, and if traffic is noted, then external device 160 waits for a clear channel before communicating.

External device 160 can be configured to allow inductive only, radio frequency only or automatic link selection in which the physical link is selected based on predetermined criteria. In one example, implantable device 110 is a slave to external device 160 implantable device 110 monitors more than one telemetry link for a command from external device 160 while in the automatic link selection mode.

When sending a table, chart or other large volume of data to implantable device 110, external device 160 operates in the command mode. In one example, each element of the table is considered a separate exchange, and thus, for a chart having ten elements, each element is transmitted as a separate exchange. In other words, a separate attempt to establish a telemetry link is commenced for each element of the table. Thus, for example, if the first element is successfully sent using inductive, then for the second element, the radio frequency telemetry link is initially attempted and if noise precludes the use of radio frequency telemetry for the second element, then an inductive telemetry link is used.

While in the command mode, external device 160 implements selective link switching in which attempts to send the data elements by first checking for a satisfactory radio frequency link and, if unsatisfactory, then using an inductive telemetry link. After a series of failed attempts to communicate using radio frequency telemetry followed by successful telemetry using the inductive telemetry link, external device 160 terminates any further attempt to use radio frequency telemetry and selects the inductive telemetry link for additional elements in the table or block of data. In one example, the series of failed attempts includes five attempts, however more or less are also contemplated. In one example, the user can force the telemetry link switch by positioning the inductive telemetry wand near implantable device 110. If the inductive telemetry link is not available (for example, the wand is not near implantable device 110), then, external device 160 continues to attempt to establish a telemetry link by alternating between inductive and radio frequency telemetry.

In one example, external device 160 selects a particular telemetry link for communicating a unit of data without alternating between possible telemetry links. For example, in a situation where the radio frequency telemetry link is unsatisfactory, then, while in command mode, external device 160 selects inductive telemetry without attempting to communicate using radio frequency telemetry.

In one example, and when operating in real time mode, external device 160 executes an algorithm to select the telemetry channel at the outset of a new frame exchange. In one example, if the current telemetry link becomes unavailable, then the physical link selection algorithm is executed.

In one example, external device 160 executes multiple attempts to establish a communication session. For example, if external device 160 issues a command to implantable device 110, external device 160 begins by transmitting a series of synchronization signals to implantable device 110. The data corresponding to the command is transmitted in the time between synchronization signals. After the command has been sent, in one example, external device 160 waits 100 milliseconds for implantable device 110 to respond. After the 100 millisecond period during which external device 160 fails to receive a response from implantable device 110, external device 160 performs a re-try procedure in which the command is sent again. The sequence of waiting and re-trying the command, in one example, is repeated seven times before terminating further attempts using the particular telemetry link. Implantable device 110 can fail to respond within the time period if the distance between devices is too great or other failure occurs.

In one example, the response time-out period is 100 milliseconds while in command mode. Therefore, since real time communication is suspended until the frame exchange is completed (that is, until the response from implantable device 110 is received), the time before changing (increasing) the frame error count may take up to the response time. External device 160 waits for the duration of the response time-out period before declaring no response from implantable device 110.

In one example, external device 160 drops the synchronization signals to assure that implantable device 110 is operating in a known state before receiving the command. By dropping the synchronization signal, any other procedure that may be executing on implantable device 110 is terminated and implantable device 110 then enters a mode conducive to receiving a command.

After sending the command, external device 160 enters a receive mode and awaits acknowledgment from implantable device 110 that confirms that the instruction was received.

In one example, external device 160 initially attempts to establish a communication session using the radio frequency telemetry link. In one example, a frame exchange is started and ended on the same physical link and thus, switching telemetry links will occur immediately prior to starting a new frame exchange or if the current telemetry link is lost during a real time telemetry session (assuming there are no other telemetry system restraints).

If the radio frequency telemetry link is unavailable, then external device 160 will attempt to start a frame exchange using the inductive telemetry link. When a telemetry channel is available (for example, radio frequency or inductive), then a frame exchange is retried once before attempting to switch telemetry links.

In one example, external device 160 will attempt telemetry link switching during a session when (a) the frame error count for the current telemetry link indicates three consecutive frame errors; (b) the frame exchange in the current telemetry link fails after being re-tried once; or (c) while using inductive telemetry link, the start of a frame exchange is issued and the radio frequency link is available (no other external device is disabling the radio frequency channel, no other radio frequency system session is in progress and the frame error count is less than three).

At the outset of a communication session with an implantable device, all telemetry systems are powered up. All systems are initially activated to allow seamless switching between different telemetry links during the session. For example, security considerations may dictate that an inductive telemetry link is used rather than a far field radio frequency telemetry link. As another example, a far field radio frequency telemetry link may be preferred rather than using a wand associated with an inductive telemetry link for communications conducted during a sterile medical procedure. In addition, reliability considerations may dictate that one telemetry system is used rather than another. Furthermore, the availability of an open communication channel may determine whether communications can be conducted using far field radio frequency telemetry or inductive telemetry.

Implantable device 110 communicates with an external device using a single telemetry link at any given time during a communication session.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An implantable apparatus comprising:
at least two implantable telemetry circuits to communicate with an external device, the at least two telemetry circuits including a first telemetry circuit to wirelessly communicate using a first wireless link and a second telemetry circuit to wirelessly communicate using a second wireless link, the first wireless link different than the second wireless link; and
an implantable controller coupled to each of the at least two telemetry circuits, the controller configured to select one of the at least two telemetry circuits for communicating, the one of the at least two telemetry circuits selected using a selection signal represented by a series of synchronization signals and wherein the selection signal is received from the external device using at least one telemetry circuit of the at least two telemetry circuits and further wherein the series of synchronization signals is periodic and each synchronization signal includes information indicative of a particular communication session.

2. The apparatus of claim 1 wherein the controller is configured to sequentially attempt to communicate using the first telemetry circuit and then using the second telemetry circuit.

3. The apparatus of claim 1 wherein the at least two telemetry circuits includes a far field telemetry circuit and a near field telemetry circuit.

4. The apparatus of claim 1 wherein the at least two telemetry circuits includes at least one of an inductive telemetry circuit and a radio frequency telemetry circuit.

5. The apparatus of claim 1 wherein the controller is configured to deselect at least one telemetry circuit of the at least two telemetry circuits concurrent with selecting the one of the at least two telemetry circuits.

6. The apparatus of claim 1 wherein selecting the one of the at least two telemetry circuits includes powering the one of the at least two telemetry circuits.

7. The apparatus of claim 1 further including at least one of a monitor circuit and a therapy circuit coupled to the controller.

8. A communication method comprising:
receiving a parameter at an external device;
using the external device, selecting a telemetry circuit from at least two telemetry circuits, each telemetry circuit configured to communicate wirelessly with an implantable device, the at least two telemetry circuits including a first telemetry circuit to communicate using a first wireless link and a second telemetry circuit to communicate using a second wireless link, the first wireless link different than the second wireless link, the telemetry circuit selected using the parameter; and
generating an instruction for the implantable device to communicate using the selected telemetry circuit, and wherein the instruction is represented by a series of synchronization signals and further wherein the series of synchronization signals is periodic and each synchronization signal includes information indicative of a particular communication session.

9. The method of claim 8 further including transmitting the instruction using the selected telemetry circuit.

10. The method of claim 8 wherein receiving the parameter includes measuring a value.

11. The method of claim 8 wherein receiving the parameter includes receiving at least one of a measure of reliability, a measure of quality, a measure of security, a measure of channel availability and a measure of data throughput associated with at least one of the first wireless link and the second wireless link.

12. The method of claim 8 wherein receiving the parameter includes receiving at least one of a user input and a condition signal from the implantable device, the parameter associated with at least one of the first wireless link and the second wireless link.

13. The method of claim 12 wherein receiving the condition signal includes receiving a battery status signal.

14. The method of claim 12 wherein receiving the user input includes receiving at least one of an indication of a preferred wireless link and an ordered list of wireless links.

15. The method of claim 8 further including:
generating a request to receive data stored in a memory of the implantable device;
sending the request to the implantable device; and
monitoring for a response using the selected telemetry circuit, wherein the selected telemetry circuit is selected using the request.

16. The method of claim 8 further including:
detecting an error while communicating using a first telemetry circuit;
terminating communications using the first telemetry circuit; and
communicating using a second telemetry circuit.

17. The method of claim 8 further including:
transmitting the instruction using the selected telemetry circuit;
monitoring for a reply using the selected telemetry circuit;
after a predetermined time, transmitting a request to communicate using an alternate telemetry circuit of the at least two telemetry circuits; and
monitoring for a reply using the alternate telemetry circuit.

18. The method of claim 8 wherein the selected telemetry circuit includes the first telemetry circuit and further including alternately attempting to communicate with the implantable device using the first telemetry circuit and the second telemetry circuit.

19. A system comprising:
an implantable device including at least two implantable telemetry circuits, each implantable telemetry circuit to communicate with an external device, the at least two implantable telemetry circuits including a first implantable telemetry circuit to wirelessly communicate using a first wireless link and a second implantable telemetry circuit to wirelessly communicate using a second wireless link, the first wireless link different than the second wireless link, the at least two implantable telemetry circuits coupled to an implantable controller configured to select one of the at least two implantable telemetry circuits for communicating, the one of the at least two implantable telemetry circuits selected using a selection signal represented by a series of synchronization signals and wherein the selection signal is received from the external device and further wherein the series of synchronization signals is periodic and each synchronization signal includes information indicative of a particular communication session; and an external device including at least one external telemetry circuit coupled to an external controller, the external controller coupled to an interface, the external device configured to generate and transmit the selection signal using a parameter received by the interface.

20. The system of claim 19 further including a memory coupled to the external controller and wherein the parameter is determined using data stored in the memory.

21. The system of claim 19 wherein the at least one external telemetry circuit includes a far field transceiver and a near field transceiver and wherein the external controller is configured to alternately monitor for a reply from the implantable device using the far field transceiver and the near field transceiver.

* * * * *